US011193993B2

(12) United States Patent
Otake et al.

(10) Patent No.: US 11,193,993 B2
(45) Date of Patent: Dec. 7, 2021

(54) RADIO FREQUENCY COIL AND MAGNETIC RESONANCE IMAGING APPARATUS USING THE SAME

(71) Applicant: HITACHI, LTD., Tokyo (JP)

(72) Inventors: Yosuke Otake, Tokyo (JP); Kohjiro Iwasawa, Tokyo (JP); Toru Shirai, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/778,931

(22) Filed: Jan. 31, 2020

(65) Prior Publication Data
US 2020/0249291 A1 Aug. 6, 2020

(30) Foreign Application Priority Data

Feb. 4, 2019 (JP) .............................. JP2019-018244

(51) Int. Cl.
| *G01R 33/34* | (2006.01) |
| *H01F 5/00* | (2006.01) |
| *A61B 5/055* | (2006.01) |
| *G01R 33/36* | (2006.01) |

(52) U.S. Cl.
CPC ........ *G01R 33/34092* (2013.01); *A61B 5/055* (2013.01); *G01R 33/36* (2013.01); *H01F 5/00* (2013.01)

(58) Field of Classification Search
CPC .. A61B 5/055; G01R 33/36; G01R 33/34092; H01F 5/00
See application file for complete search history.

(56) References Cited

U.S. PATENT DOCUMENTS

| 4,887,038 A | * | 12/1989 | Votruba | ............... | G01R 33/341 |
| | | | | | 324/318 |
| 5,327,898 A | * | 7/1994 | Yoshino | ............. | G01R 33/3678 |
| | | | | | 324/318 |
| 5,477,146 A | * | 12/1995 | Jones | ............... | G01R 33/34046 |
| | | | | | 324/318 |
| 6,169,400 B1 | * | 1/2001 | Sakuma | ........... | G01R 33/34053 |
| | | | | | 324/318 |
| 6,326,789 B1 | * | 12/2001 | Yoshida | ............. | G01R 33/3415 |
| | | | | | 324/307 |
| 7,212,002 B2 | * | 5/2007 | Greim | .................. | G01R 33/341 |
| | | | | | 324/318 |

(Continued)

FOREIGN PATENT DOCUMENTS

JP 4820022 B2 1/2003

*Primary Examiner* — Dixomara Vargas
(74) *Attorney, Agent, or Firm* — Volpe Koenig

(57) ABSTRACT

A flexible RF coil with excellent portability is provided. The RF coil includes a first coil, a first skeleton, and a second skeleton, the first skeleton and the second skeleton being rod shaped. The first coil includes a first loop made from a conductor that receives radio frequency signals, and a first signal detector that is inserted in series into the first loop and that detects the signals received by the first loop. The first skeleton and the second skeleton are arranged with a spacing in the short axis direction, the first signal detector is mounted on the first skeleton, and a portion of the first loop that faces the first signal detector is mounted on the second skeleton. The first loop is deformable, and the spacing between the first skeleton and the second skeleton is changeable in accordance with the deformation of the first loop.

16 Claims, 11 Drawing Sheets

(56) References Cited

U.S. PATENT DOCUMENTS

| | | | | |
|---|---|---|---|---|
| 7,443,163 B2* | 10/2008 | Warntjes | G01R 33/3657 | 324/318 |
| 7,696,752 B2* | 4/2010 | Takamori | G01R 33/3415 | 324/307 |
| 7,965,081 B2* | 6/2011 | Kundner | G01R 33/341 | 324/318 |
| 9,517,021 B2* | 12/2016 | Anderson | A61B 5/0002 | |
| 10,653,335 B2* | 5/2020 | Dohata | G01R 33/34084 | |
| 2003/0076101 A1* | 4/2003 | Sakuma | G01R 33/34046 | 324/318 |
| 2007/0262777 A1* | 11/2007 | Warntjes | G01R 33/3657 | 324/318 |
| 2009/0012389 A1* | 1/2009 | Kundner | G01R 33/28 | 600/422 |
| 2010/0272229 A1* | 10/2010 | Biber | G01R 33/34007 | 378/20 |
| 2014/0361769 A1* | 12/2014 | Hardie | G01R 33/34 | 324/307 |
| 2015/0087966 A1* | 3/2015 | Anderson | A61B 5/0002 | 600/415 |
| 2016/0135711 A1* | 5/2016 | Dohata | G01R 33/3664 | 600/422 |
| 2019/0162800 A1* | 5/2019 | Schnell | G01R 33/34084 | |

* cited by examiner

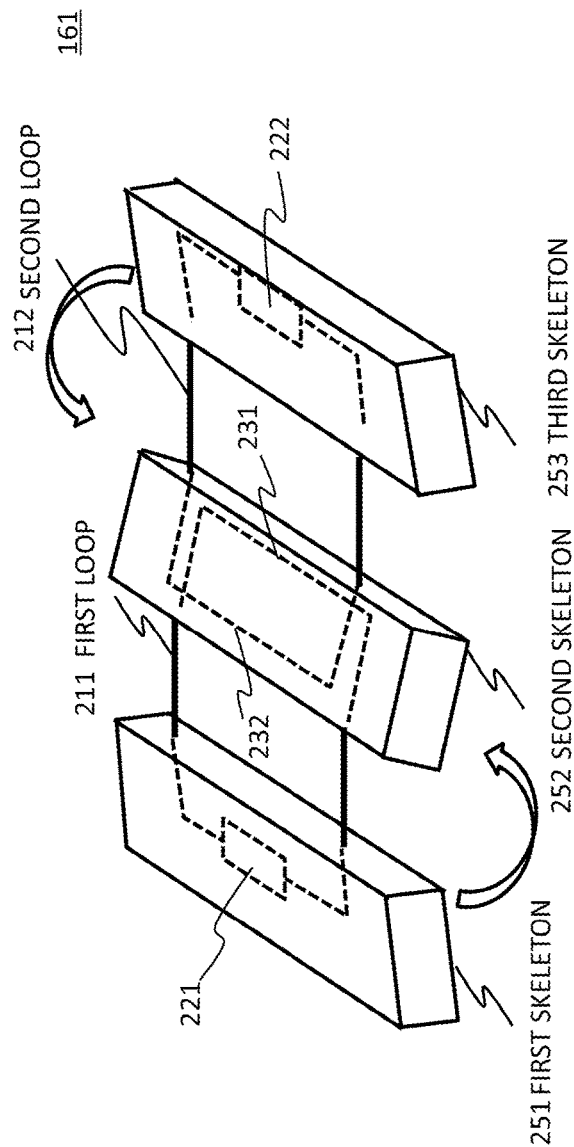
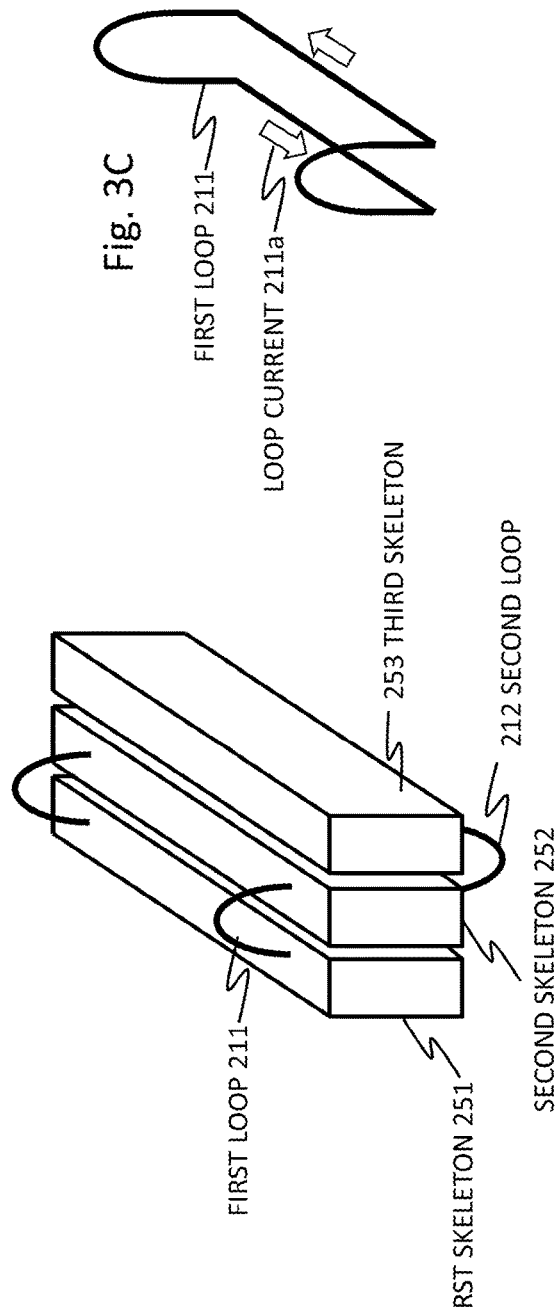

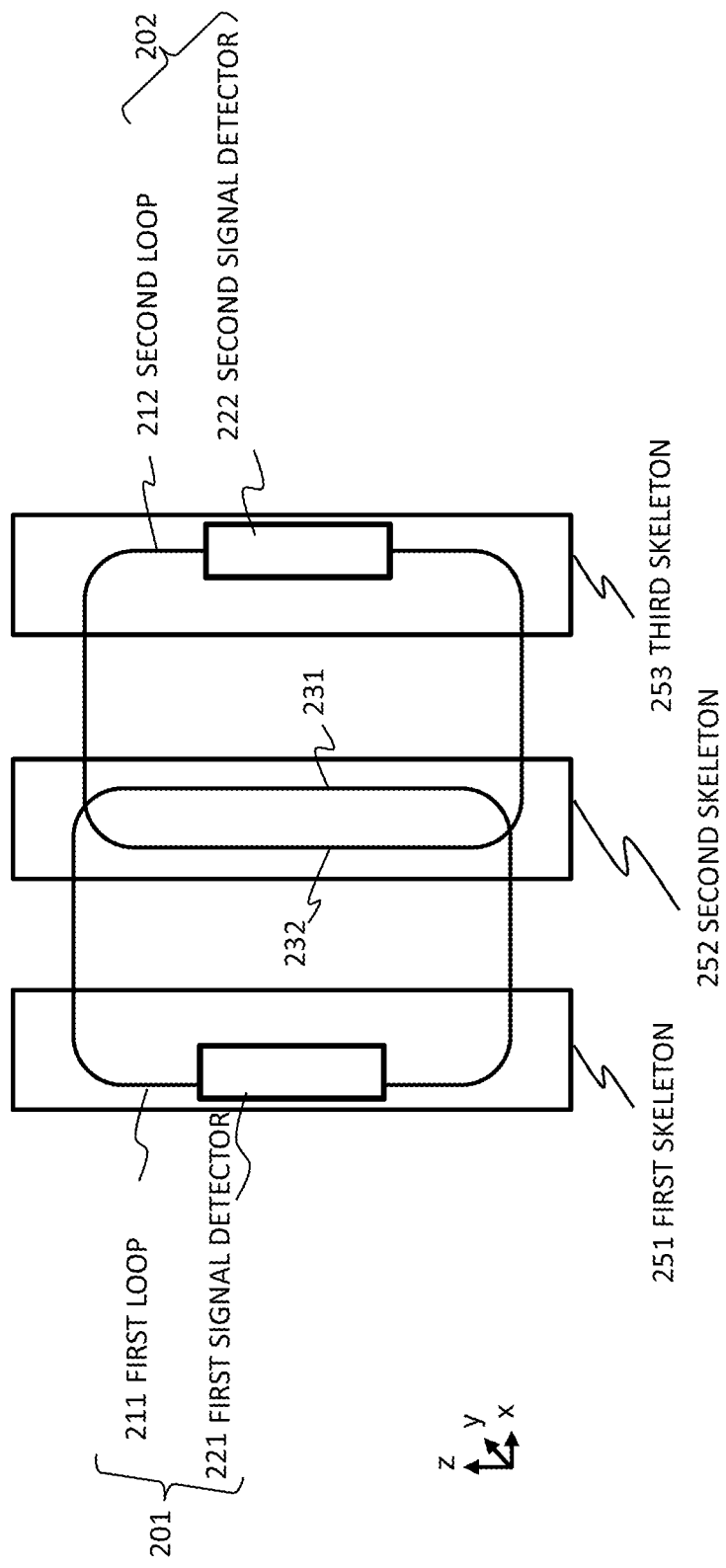

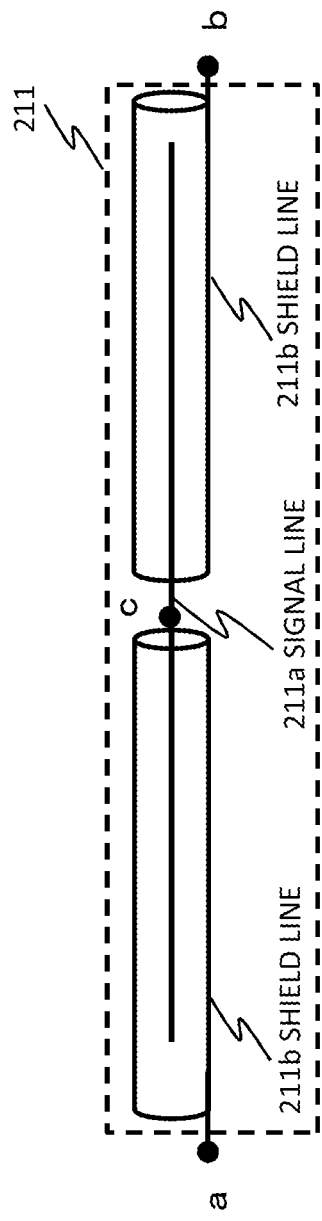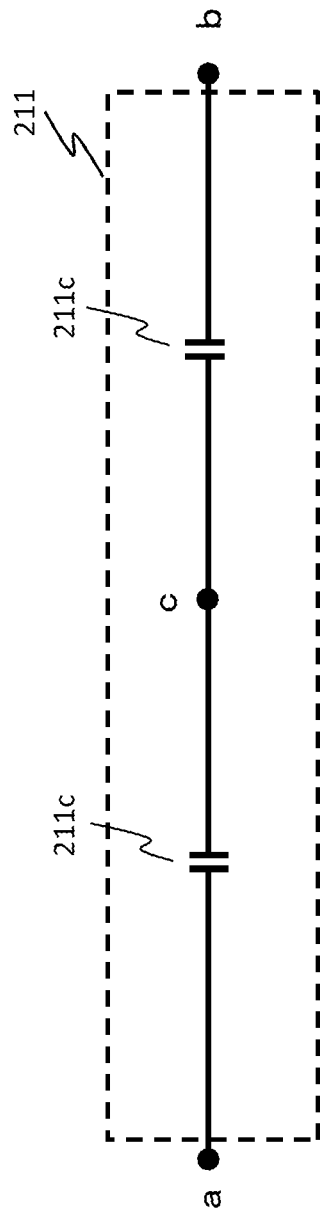
Fig. 6A
Fig. 6B

RADIO FREQUENCY COIL AND MAGNETIC RESONANCE IMAGING APPARATUS USING THE SAME

BACKGROUND OF THE INVENTION

Field of the Invention

The present invention relates to a radio frequency coil that is used in a magnetic resonance imaging (MRI) apparatus.

Background Art

MRI apparatuses irradiate subjects with radio frequency magnetic fields and receive nuclear magnetic resonance signals produced by the subject. MRI apparatuses include radio frequency coils (hereinafter also referred to as "RF coils"). In order to achieve high quality images, separate coils are used for the irradiation-use RF coil and the receiving-use RF coil.

At present, a multi-channel coil is commonly used as the receiving-use RF coil (hereinafter referred to as the "receiving RF coil"). This multi-channel coil includes 32 to 128 coils (ch) in order to realize a high SNR and high-speed imaging. Each coil of the receiving RF coil includes a coil element made from a conductor, a capacitor that adjusts the resonance frequency of the coil, a signal detection circuit that detects the current that flows through the coil, a frequency adjustment circuit that changes the resonance frequency of the RF coil, and a magnetic coupling prevention circuit that prevents magnetic coupling with the other coils. The frequency adjustment circuit adjusts the resonance frequency of the receiving RF coil to the same frequency as the nuclear magnetic resonance signal, thereby enabling the receiving RF coil to acquire the resonance frequency signal. The signal detection circuit, the magnetic coupling prevention circuit, and the frequency adjustment circuit include electronic components such as inductors, capacitors, and diodes.

From the perspective of obtaining high sensitivity, it is preferable that the receiving RF coil is arranged near the subject. As such, receiving RF coils with various shapes have been manufactured so as to conform to the various parts of the body of the subject. There are rigid-type receiving RF coils and flexible-type receiving RF coils. Rigid-type receiving RF coils are disposed inside a resin housing that has a shape that conforms to the body part of the subject. Flexible-type receiving RF coils are also disposed in a resin housing, but a portion of the resin housing has a flexible shape and can be made to conform to the shape of the subject as desired. An operator selects the RF coil that is optimal for the part of the subject to be imaged, and arranges the selected RF coil on the part to be imaged.

With flexible-type receiving RF coils, the portion that covers the signal detection circuit, or other circuits that include electronic components, is protected by a comparatively hard and heavy resin housing in order to prevent the electronic components from being destroyed by external impact. The coil element exhibits flexibility and, as such, is provided outside the resin housing or the protective cover, but is covered and protected by a sponge in order to prevent the conductor from breaking due to metal fatigue.

Patent Literature 1 proposes a technique for reducing the number of components of the receiving RF coil and imparting flexibility by using a coaxial cable as the conductor of the coil element.

CITATION LIST

Patent Literature

Patent Literature 1: Japanese Patent No. 4820022

SUMMARY OF THE INVENTION

The resin housing portion of conventional receiving RF coils is comparatively heavy and, also, has hardly any flexibility. In addition, the sponge that covers the coil element conductor in the housing reduces the flexibility of the receiving RF coil.

Multi-channel coils require a signal detection circuit, a frequency adjustment circuit, and a magnetic coupling prevention circuit for each coil. As such, multiple electronic components are installed and all of these electronic components are covered by the resin housing. Consequently, the weight of the receiving RF coil is typically about 2 to 5 kg. In addition, the housing of the receiving RF coil covers the part to be imaged of the subject without deforming and, as such, has a pre-designed three-dimensional shape. Due to this, the receiving RF coil has poor portability, occupies a large volume when stored, and requires a large storage location. Since abdominal coils and similar receiving RF coils for large parts to be imaged are particularly large and heavy, the operator carries the abdominal receiving RF coil with both hands and the work to arrange the receiving RF coil on the abdomen of the subject is a large burden.

Even when a coaxial cable is used as the coil element conductor as in Patent Literature 1, frequency adjustment circuits must be used and, as such, the receiving RF coil still includes multiple electronic components and the protective cover is needed. As such, there are limits to improvements in weight reduction and flexibility.

Moreover, even if the weight of abdominal coils and similar receiving RF coils for large parts to be imaged could be reduced, such coils are large and, as such, handleability is poor and usability such as storability and portability will not be improved.

One objective of the present invention is to provide a flexible RF coil with excellent portability.

A RF coil that achieves the objective described above includes a first coil, a first skeleton, and a second skeleton, the first skeleton and the second skeleton being rod shaped. The first coil includes a first loop made from a conductor that receives radio frequency signals, and a first signal detector that is inserted in series into the first loop and that detects the signals received by the first loop. The first skeleton and the second skeleton are arranged with a spacing in the short axis direction (that is, so that long axes of the first skeleton and the second skeleton face each other), the first signal detector is mounted on the first skeleton, and a portion of the first loop that faces the first signal detector is mounted on the second skeleton. The first loop is deformable, and the spacing between the first skeleton and the second skeleton is changeable in accordance with deformation of the first loop.

According to the present invention, a flexible RF coil can be provided that has excellent portability and that can be folded so as to bring the first skeleton and the second skeleton close to each other.

BRIEF DESCRIPTION OF THE DRAWINGS

FIG. 3A is a perspective view of a receiving RF coil according to the embodiment, illustrating the receiving RF coil in an expanded state;

FIG. 3B is a perspective view of the receiving RF coil, illustrating the receiving RF coil in a folded state;

FIG. 3C is a drawing explaining loop current while the receiving RF coil is in the folded state;

FIG. 4 is a block diagram illustrating the structure of the receiving RF coil according to the embodiment;

FIG. 6A is a block diagram illustrating an example in which a loop forming the receiving RF coil according to the embodiment is constituted by a coaxial cable;

FIG. 6B is an equivalent circuit diagram of the coaxial cable of FIG. 6A;

DETAILED DESCRIPTION OF THE INVENTION

Hereinafter, a radio frequency coil of an embodiment of the present invention and an MRI apparatus that uses the radio frequency coil are described using the drawings. The present invention is not limited to the following embodiments, and the design thereof can be freely modified within the scope of the objective of the present invention. All such modifications are encompassed within the scope of the present invention.

Overall Structure of MRI Apparatus

The overall structure of an MRI apparatus 100 according to the present embodiment will be described while referencing FIGS. 1 and 2.

Figure 1:
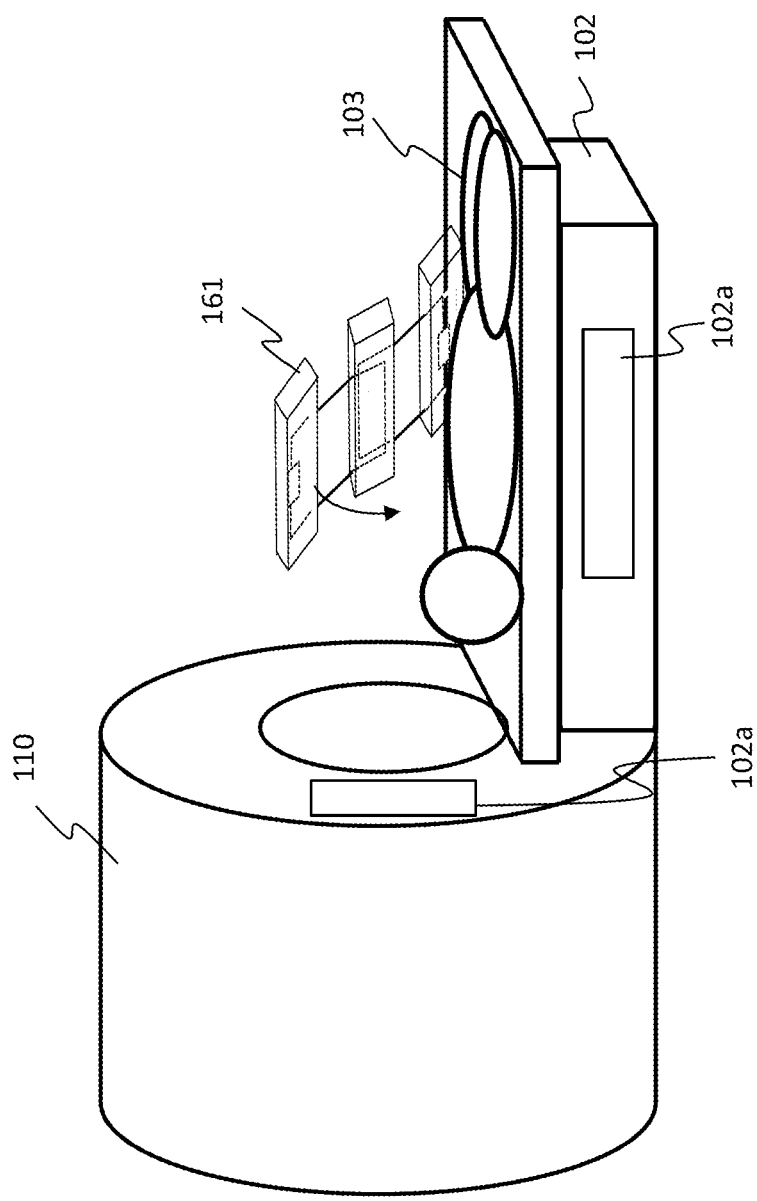
FIG. 1 is a perspective view of an example of an MRI apparatus according to an embodiment.
Figure 2:
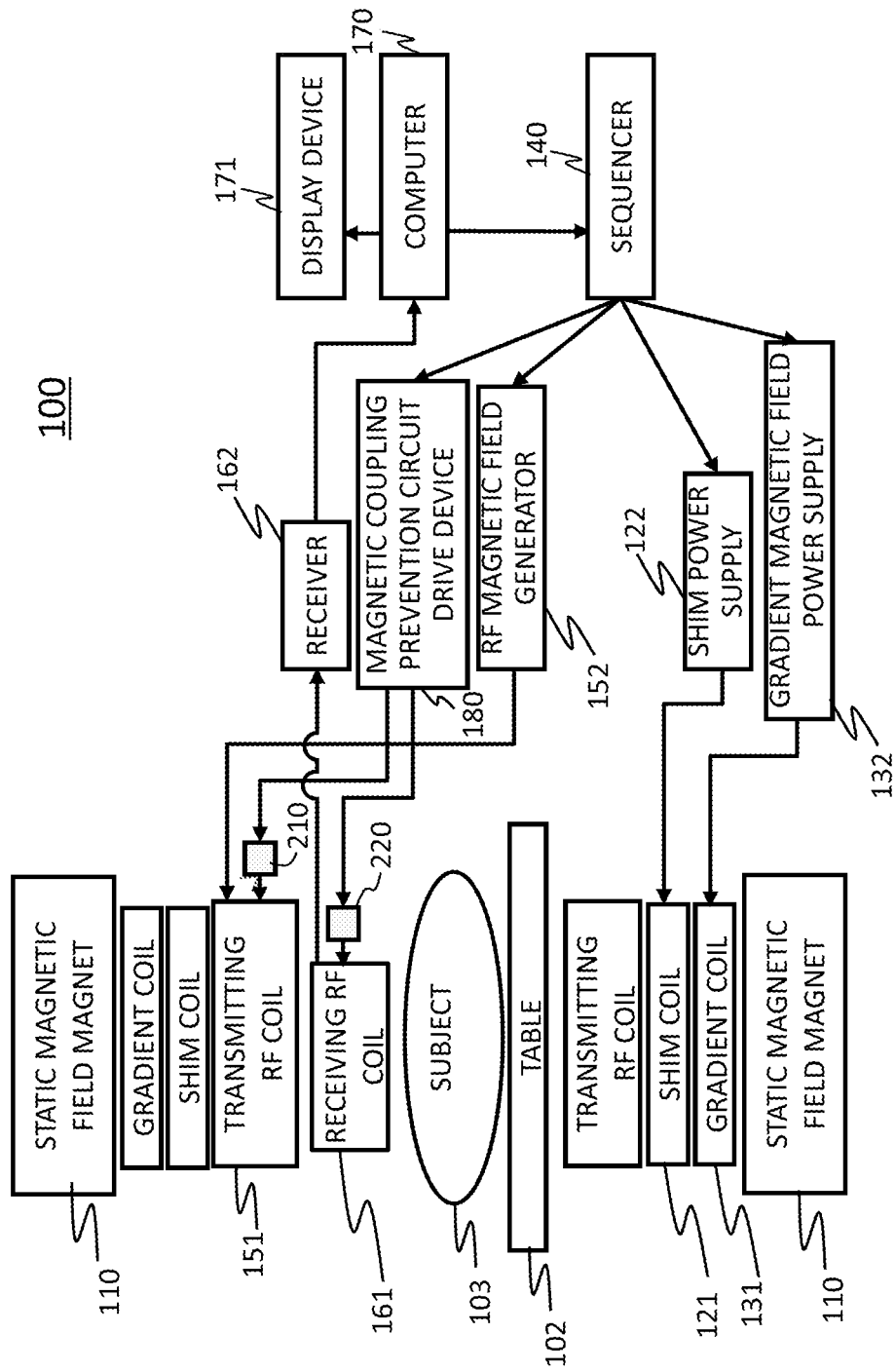
FIG. 2 is a block diagram illustrating the structure of the MRI apparatus according to the embodiment.

FIG. 1 illustrates the appearance of an example of the MRI apparatus, and FIG. 2 illustrates the schematic structure of the entire MRI apparatus.

As illustrated in FIGS. 1 and 2, the MRI apparatus 100 includes a static magnetic field magnet 110, a gradient coil 131, a transmitting RF coil 151, a receiving RF coil 161, a gradient coil power supply 132, a shim coil 121, a shim power supply 122, an RF magnetic field generator 152, a receiver 162, a magnetic coupling prevention circuit drive device 180, a computer 170, a sequencer 140, and a display device 171. Note that reference symbol 102 is a table on which the part to be imaged of a subject 103 is placed in imaging space.

The static magnetic field magnet 110 generates a static magnetic field in the imaging space. FIG. 1 illustrates an appearance in which a tunnel magnet, which generates a horizontal static magnetic field by a solenoid coil, is used as the static magnetic field magnet 110. However, a static magnetic field magnet 110 that generates a vertical static magnetic field may also be used.

The gradient coil 131 is connected to the gradient coil power supply 132 and generates a gradient magnetic field in the imaging space. The shim coil 121 is connected to the shim power supply 122 and adjusts the uniformity of the static magnetic field.

The transmitting RF coil 151 is connected to the RF magnetic field generator 152 and irradiates (transmits) an RF magnetic field on the subject 103. The frequency of the RF magnetic field is set to a frequency that excites the nuclear magnetism of the nuclei (protons and the like) of the nuclides of the subject 103 to be imaged. Any structure may be used for the transmitting RF coil 151. For example, a birdcage-type RF coil can be implemented as the transmitting RF coil 151.

The receiving RF coil 161 is connected to the receiver 162 and receives the nuclear magnetic resonance signals from the subject 103. In this case, a multi-channel RF coil formed from a plurality of coil units (hereinafter referred to as "coil array") is implemented as the receiving RF coil 161 according to the present embodiment. In the following description, the number of coils of the coil array is referred to as the "number of channels."

As illustrated in FIGS. 1 and 3A, the receiving RF coil 161 according to the present embodiment has a deformable structure, and can be used by being wrapped on the part to be imaged of the subject 103. As illustrated in FIG. 3B, the receiving RF coil 161 can be folded in a bellows-like manner when not being used, and can be easily carried. A detailed description of the structure of the receiving RF coil 161 will be given later.

Magnetic coupling prevention circuits 210 and 220 are respectively connected to the transmitting RF coil 151 and the receiving RF coil 161. The magnetic coupling prevention circuit drive device 180 is connected to the magnetic coupling prevention circuits 210 and 220 and prevents magnetic coupling between the transmitting RF coil 151 and the receiving RF coil 161.

The sequencer 140 sends commands to the gradient coil power supply 132, the RF magnetic field generator 152, and the magnetic coupling prevention circuit drive device 180, and causes each of the gradient coil power supply 132, the RF magnetic field generator 152, and the magnetic coupling prevention circuit drive device 180 to operate. The commands are sent in accordance with instructions from the computer 170. Moreover, in accordance with an instruction from the computer 170, the sequencer 140 sets a magnetic resonance frequency, which serves as a reference for demodulation, in the receiver 162. Specifically, when imaging, the gradient coil 131 and the transmitting RF coil 151 respectively irradiate a gradient magnetic field and a RF magnetic field on the subject 103 at Predetermined timings in accordance with commands from the sequencer 140. The nuclear magnetic resonance signals generated by the subject 103 are detected by the receiving RF coil 161, and demodulation is performed by the receiver 162.

The computer 170 controls the operations of the entire MRI apparatus 100 and carries out various types of signal processing. For example, the computer 170 receives the signal demodulated by the receiver 162 via an A/D conversion circuit (not illustrated in the drawings) and carries out signal processing such as image reconstruction. The results of that processing are displayed on the display device 171. The demodulated signal and measurement conditions are, as desired, saved on a storage medium. Moreover, the computer 170 sends commands to the sequencer 140 so that the various devices operate at pre-programmed timings and intensities. Furthermore, when the static magnetic field uniformity requires adjustment, the computer 170 sends a command to the shim power supply 122 via the sequencer 140, and uses the shim coil 121 to adjust the static magnetic field uniformity.

Receiving RF Coil

Next, the receiving RF coil 161 according to the present embodiment will be described while referencing FIGS. 3 to 7.

As illustrated in FIGS. 3A and 4, the receiving RF coil 161 is a two-channel array coil in which a first coil 201 and a second coil 202 are juxtaposed. In addition to the first and second coils 201 and 202, the receiving RF coil 161 also includes three rod-shaped skeletons 251, 252, and 253 that support portions of the first and second coils 201 and 202.

The first and second coils 201 and 202 respectively include loops 211 and 212 made from conductors that receive radio frequency signals, and signal detectors 221 and 222 that are inserted in series into the loops 211 and 212 and that detect the signals received by the loops 211 and 212.

The three skeletons 251, 252, and 253 are juxtaposed in the short axis direction with a spacing therebetween. The signal detectors 221 and 222, which are respectively inserted in the loops 211 and 212, are juxtaposed in the short axis direction of the skeletons 251 and the like with a spacing therebetween, and each of the signal detectors 221 and 222 is supported by one of the skeletons. Specifically, the first signal detector 221 of the coil 201 is supported by the skeleton 251, and the signal detector 222 of the coil 202 is supported by the skeleton 253.

The loops 211 and 212 are deformable. Since the signal detectors 221 and 222 are mounted on the skeletons 251 and 253, only the loops 211 and 212 bridge the spaces between the skeletons 251, 252, and 253, and there are no signal detection circuits or other circuits in the spaces between the skeletons 251, 252, and 253. Therefore, the loops 211 and 212 between the skeletons 251, 252, and 253 can be deformed and, as illustrated in FIG. 1, closely arranged so as to wrap along the part to be imaged of the subject 103. Thus, the receiving RF coil 161, which is in close contact with the subject 103, can more efficiently receive the nuclear magnetic resonance signals emitted from the subject 103.

The loops 211 and 212 are deformable, only the loops 211 and 212 are disposed in the spaces between the skeletons, and no circuits are disposed in the spaces between the skeletons. As a result of this configuration, as illustrated in FIG. 3B, the skeletons 251 and 252 can be folded like bellows and made adjacent to each other by reducing the spaces between the skeletons 251, 252, and 253 while deforming the loops 211 and 212 until the loops 211 and 212 are bent. As a result, a user can carry the receiving RF coil in the folded state illustrated in FIG. 3B to the part to be imaged of the subject 103 and, as such, portability is excellent. Additionally, the receiving RF coil can be stored in the folded state and, as such, can be stored in a small space and has excellent storability.

The receiving RF coil 161 folds in a bellow-like manner as illustrated in FIG. 3B, which results in the first loop 211 and the second loop 212 each taking the shape of two adjacent parallel lines as illustrated in FIG. 3C. As a result, current 211a flowing through the loop always flows backward through the two adjacent parallel lines, and the magnetic fields generated from the lines cancel each other out. Thus, on whole, the loops do not generate magnetic fields.

Accordingly, magnetic interference will not occur between that coil and other coils when stored and, as such, limitations on the storage location are eliminated. Moreover, since the performance of the other coils will not be degraded, the operator can always acquire high-quality images.

In one example, coaxial cables, which are covered with an insulating material, are implemented as the loops 211 and 212. However, configurations are possible in which components obtained by covering conductors with insulating material are used as the loops 211 and 212.

The rod-shaped skeletons 251, 252, and 253 can be formed from a sponge material that is hard enough to be able to be self-supporting. As a result of this configuration, the rod-shaped skeletons 251, 252, and 253 can reduce the weight of the receiving RF coil 161. In addition, by forming the skeletons 251, 252, and 253 from a sponge material, the skeletons 251, 252, and 253 can also be bent in the long axis direction. As a result, the receiving RF coil can be arranged so as to closely conform to the body of the subject 103 in the long axis direction as well.

Next, a more detailed description of the receiving RF coil 161 will be given.

The first skeleton 251 and the second skeleton 252 of the receiving RF coil 161 are arranged with a spacing in the short axis direction. The third skeleton 253 is arranged on the side of the second skeleton 252 opposite the first skeleton 251, and is arranged with a spacing with the second skeleton 252 in the short axis direction of the skeletons. In this case, the three skeletons 251, 252, and 253 are arranged such that the long axes thereof are parallel to each other.

The first signal detector 221, which is inserted in series into the first loop 211 of the first coil 201, is mounted (fixed) on the first skeleton 251. A portion 231 of the first loop 211 that faces the first signal detector 221 is mounted (fixed) on the second skeleton 252.

The second signal detector 222, which is inserted in series into the second loop 212 of the second coil 202, is mounted (fixed) on the second skeleton 252 or the third skeleton 253 (in this case, on the third skeleton 253). A portion 232 of the second loop 212 that faces the second signal detector 222 is mounted (fixed) on the skeleton of the second skeleton 252 and the third skeleton 253 on which the second signal detector 222 is not mounted (in this case, on the second skeleton 252).

The first loop 211 and the second loop 212 each include a structure or a circuit that removes magnetic coupling between the first loop 211 and the second loop 212. For example, as illustrated in FIG. 4, in order to remove magnetic coupling, the first loop and the second loop are arranged such that the portions on the second skeleton 252 overlap at a predetermined area ratio (for example, 10%).

In another example of a structure that removes magnetic coupling, the first loop 211 and the second loop 212 may be arranged so as to face each other on the second skeleton 252, and inductors may be inserted into the loops 211 and 212 at opposing positions. In another example of a structure that removes magnetic coupling, a circuit configuration may be used in which a capacitor is disposed on the second skeleton 252, and the capacitor is inserted in series into both the first loop 211 and the second loop 212. Using the inductors facilitates the adjustment of the magnetic coupling removal and, as such, simplifies manufacturing work. In addition, using a capacitor enables magnetic coupling with suppressed conductor loss and improves sensitivity.

Note that, when the magnetic coupling between coils is weak, the structure that removes magnetic coupling may be omitted. The receiving RF coil 161 can be made lighter by eliminating unnecessary circuits.

Next, detailed examples of circuit configurations of each of the coils 201 and 202 will be described while referencing FIGS. 5 and 6. The circuit configurations of the first coil 201 and the second coil 202 are the same. As such, only a description of the first coil 201 is given.

Figure 5:
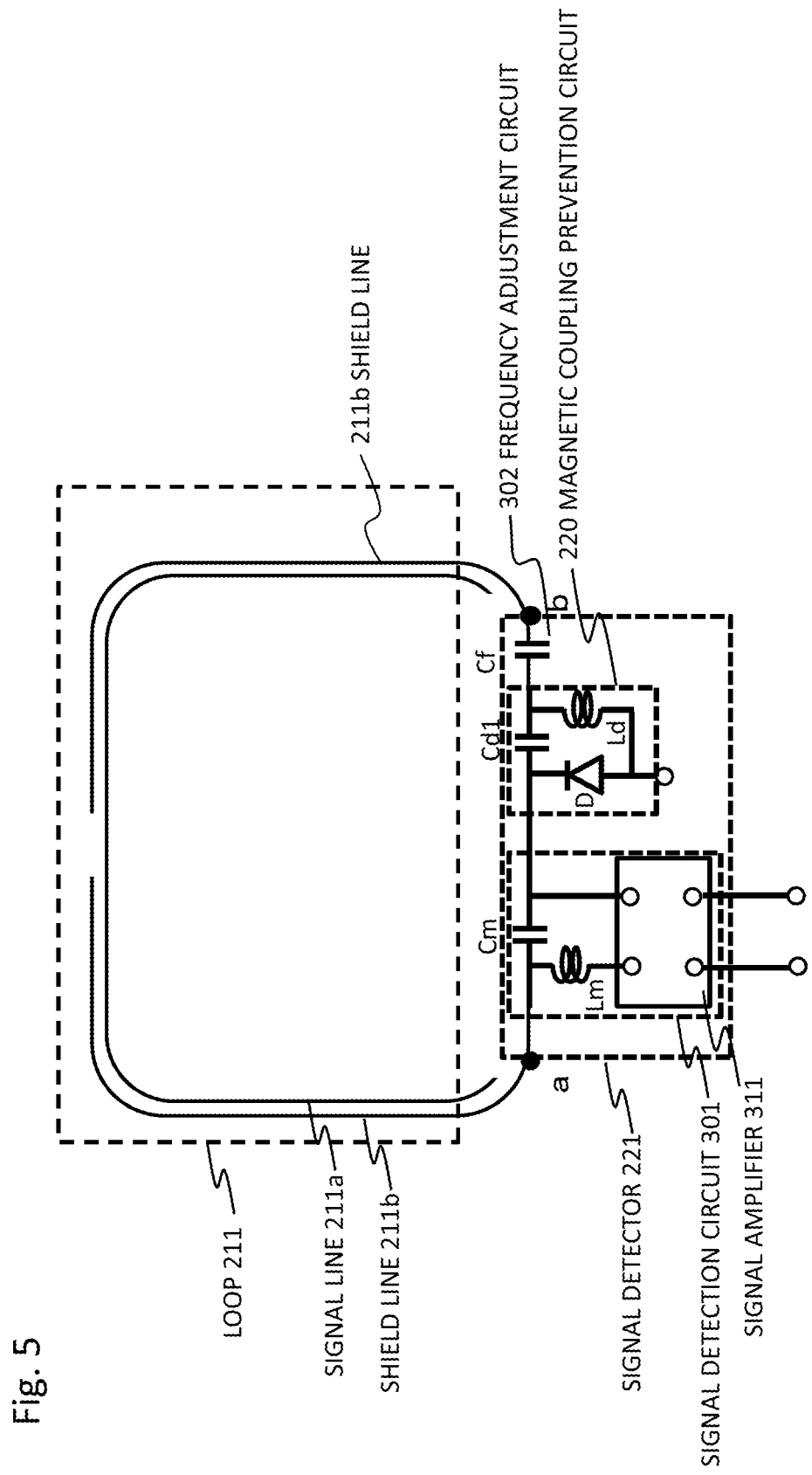
FIG. 5 is a circuit diagram of the receiving RF coil according to the embodiment.

As illustrated in FIG. 5, the first loop 211 is constituted by a coaxial cable that includes a signal line 211a and a shield line 211b. As illustrated in FIG. 6A, the shield line 211b of the coaxial cable is broken and insulated at a middle position in the length direction of the cable. Thus, as illustrated in FIG. 6B, from the perspective of terminals a and b, a circuit configuration is obtained that is equivalent to inserting capacitors 211c into the loop 211 of the coaxial cable.

The signal detector 221 is inserted in series into the loop 211. The shield lines 211b on both ends of the coaxial cable that constitutes the loop 221 are connected to the signal detector 221.

The signal detector 221 includes a signal detection circuit 301, the magnetic coupling prevention circuit 220, and a frequency adjustment circuit (Cf) 302, and each of the capacitors Cm, Cd1, and Cf are connected in series.

The signal detection circuit 301 includes a first capacitor (Cm), a first inductor (Lm), and a signal amplifier 311. The first inductor (Lm) and the signal amplifier 311 are connected in series to form a first series circuit. The first series circuit is connected in parallel to the first capacitor (Cm). The first coil 201 is adjusted by adjusting the value of the first capacitor (Cm) to an input impedance that minimizes the noise generated when the signal amplifier 311 is connected. Furthermore, the first inductor (Lm) is adjusted such that the frequency of the parallel circuit consisting of the first series circuit and the first capacitor (Cm) is the same as the magnetic resonance frequency, thereby preventing magnetic coupling with other coils.

The magnetic coupling prevention circuit 220 includes a second capacitor (Cd1), a diode (D), and a second inductor (Ld). The second inductor (Ld) and the diode (D) are connected in series to form a second series circuit. The second series circuit is connected in parallel to the second capacitor (Cd1). The diode (D) is connected to the magnetic coupling prevention circuit drive device 180. When the diode (D) is ON, a parallel resonance circuit consisting of the second capacitor (Cd1), the second inductor (Ld), and the diode (D) matches the resonance frequency to the resonance frequency of the transmitting RF coil, which is adjusted to the same frequency as the magnetic resonance frequency. As a result, magnetic coupling between the transmitting RF coil and the receiving RF coil is prevented.

The frequency adjustment circuit 302 is constituted from a frequency adjustment capacitor (Cf). The frequency adjustment circuit 302 is adjusted such that the circuit of the entire first coil 201, as viewed from the signal amplifier 311, resonates at the frequency of the nuclear magnetic resonance signals. As a result, the first coil 201 can receive the nuclear magnetic resonance signals.

With conventional receiving RF coils, the capacitors are inserted on the loop, thereby necessitating a hardcover to protect the circuits. However, the coil illustrated in FIGS. 5 and 6 achieves the equivalent of capacitors by the structure of the coaxial cable, thus eliminating the need for a hard cover. As a result, greater flexibility compared to conventional coils is obtained. Moreover, since the loop 211 is constituted by the coaxial cable, which has excellent flexibility with respect to bending, there is no need to use the sponge that protects the conductor in conventional coils. As a result, the receiving RF coil according to the present embodiment is highly flexible.

Next a description is given of improvements, compared to conventional receiving RF coils, of the storability and the portability of the receiving RF coil according to the present embodiment.

Since the RF coil according to the present embodiment does not include a sponge or resin housing, flexibility greater than that of conventional multi-channel RF coils can be obtained. In addition, as illustrated in FIGS. 3A and 4, the signal detectors 221 and 222 are arranged on the first and third skeletons 251 and 253. As such, the inflexible protective covers that protect the electric circuit components are only disposed on the skeletons. As a result of this configuration, the flexibility of the loops 211 and 212 between the skeletons improves.

Thus, as illustrated in FIG. 3B, the receiving RF coil according to the present embodiment can be folded such that the skeletons 251, 252, and 253, which were arranged substantially parallel, become adjacent to each other. As a result, the receiving RF coil becomes compact, and the storability and the portability of the receiving RF coil improve.

The signal detectors and portions of the loops of all of the coils of the RF coil according to the present embodiment are supported by the juxtaposed skeletons, and the distance between the skeletons enables the loops to be bent in half. As a result of this configuration, it is possible to fold the receiving RF coil with alternating mountains and valleys in the short axis direction of the receiving RF coil skeletons 251, 252, and 253, thereby obtaining a bellows-like shape. Therefore, when returning the receiving RF coil to the original expanded shape, the receiving RF coil can be expanded by simply pulling the skeletons 251 and 253 on both ends so as to separate from each other. As such, work is easier and operability is excellent.

Since, as illustrated in FIG. 3C, the loops 211 and 212 are bent so as to be folded in half, the loops 211 and 212 become two adjacent parallel lines. As a result, magnetic fields are not generated and the magnetic flux of other receiving RF coils is less likely to enter the loops 211 and 212. Thus, even if there are other coils nearby, it is less likely that interfere will occur. Therefore, a wider range of storage location candidates is obtained.

Since a slightly flexible sponge material that is self-supporting can be used as the skeletons 251, 252, and 253, the skeletons 251, 252, and 253 can slightly deform when pressure is applied. As such, the receiving RF coil can be arranged so as to conform to the subject, and sensitivity improves.

A drawing mechanism may be provided so as to simply compact the receiving RF coil according to the present embodiment. In one example, at least a portion of the loops 211 and 212 can be formed from a conductor that has shape memory characteristics. By causing the conductor that has shape memory characteristics to remember the compacted form (the shape illustrated in FIG. 3B), the receiving RF coil can be configured to return to the compact shape due to the shape memory characteristics by placing the skeletons 251, 252, and 253 in a free state.

Figure 7:
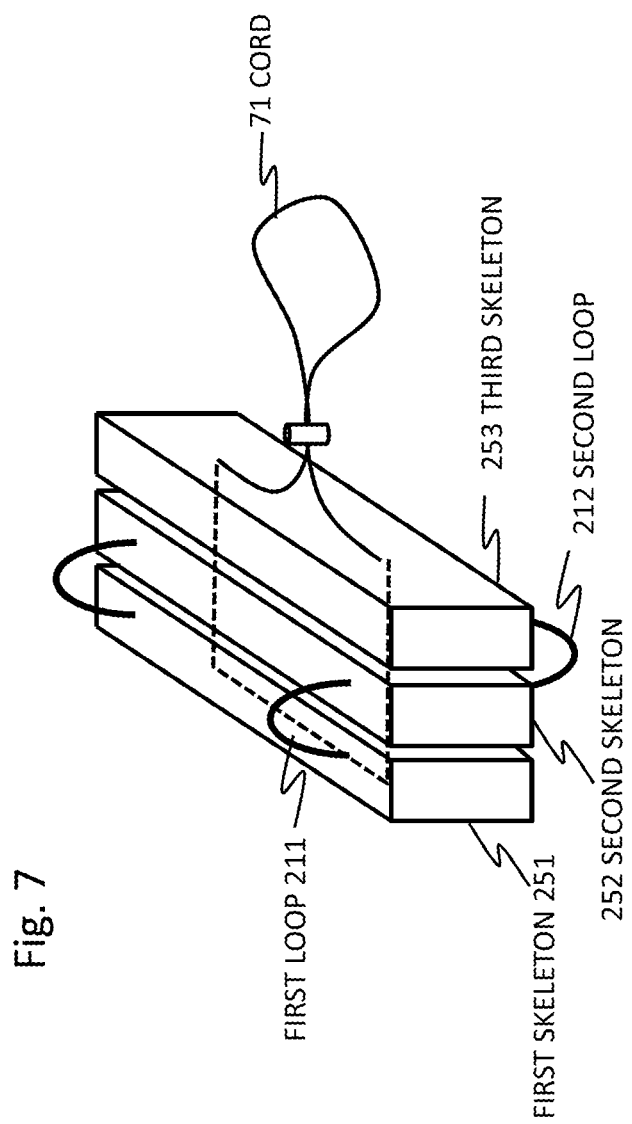
FIG. 7 is a perspective view illustrating a configuration in which a cord 71 is passed through the receiving RF coil of the embodiment as a drawing mechanism of the receiving RF coil.
Figure 9:
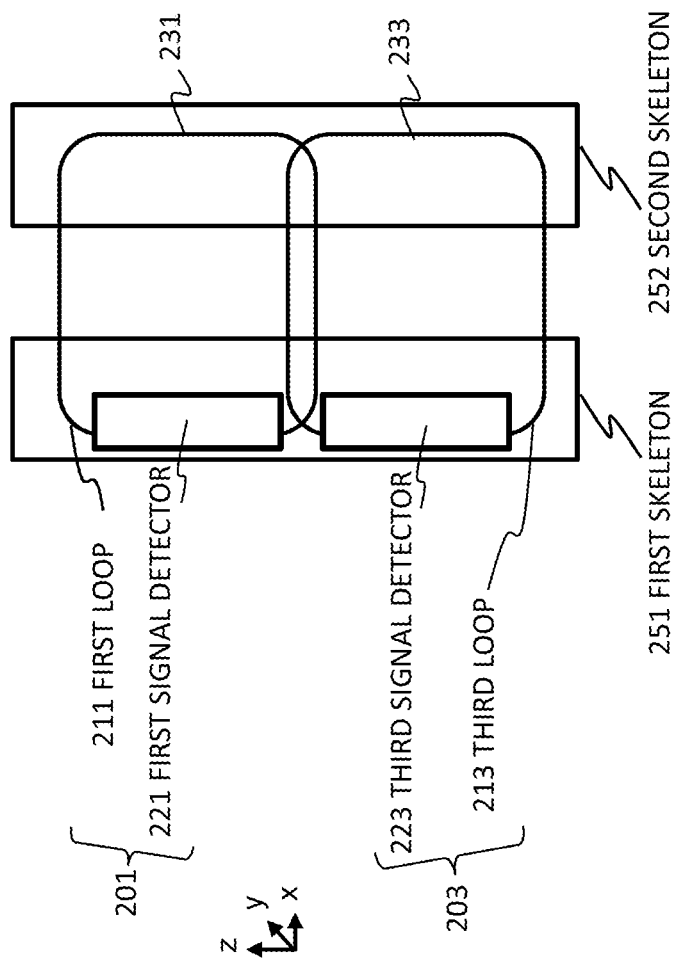
FIG. 9 is a block diagram of a receiving RF coil according to Modified Example 2 of the embodiment.

In another example, as illustrated in FIG. 7, a cord disposed so as to sew all of the skeletons together (so as to pass through the first second and third skeletons) may be provided as the drawing mechanism. As illustrated in FIG. 9, all of the skeletons 251, 252, and 253 can made adjacent by moving the skeletons along the cord 71, and the receiving RF coil can be arranged in a compact shape by a single operation. Thus, the work of compacting becomes easier, which improves operability.

Modification Example 1

Figure 8:
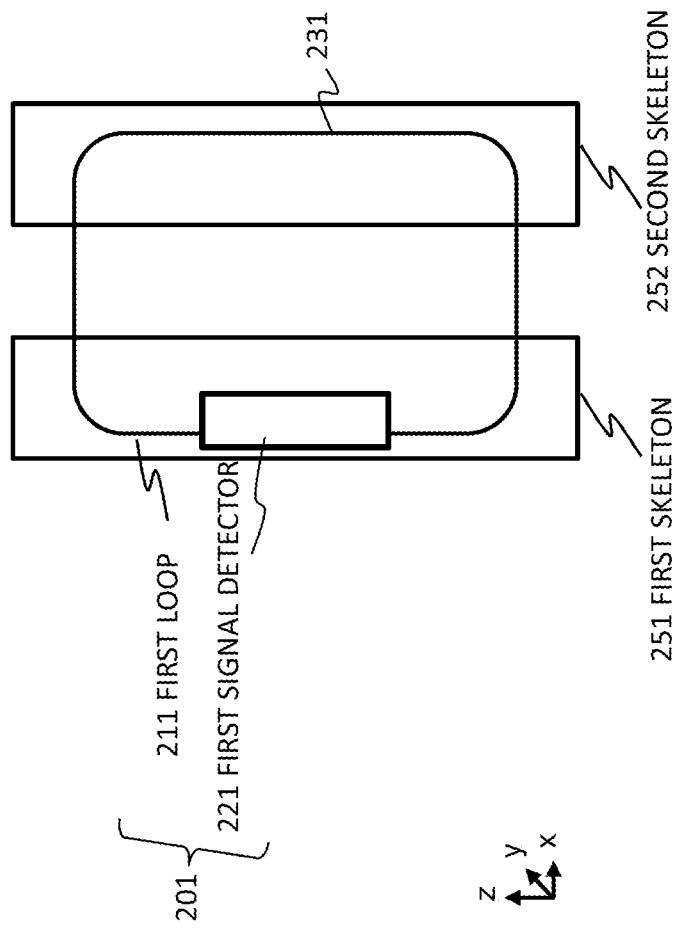
FIG. 8 is a block diagram of a receiving RF coil according to Modified Example 1 of the embodiment.

With the receiving RF coil according to the embodiment described above, a configuration was described in which the two coils 201 and 202 are supported by the three skeletons 251, 252, and 253. However, as illustrated in FIG. 8, a configuration is possible in which one coil 201 is supported using two skeletons 251 and 252. Specifically, in this configuration, the first signal detector 221 is mounted on the first skeleton 251, and a portion 231 of the first loop 211 that faces the first signal detector 221 is mounted on the second skeleton 252.

The receiving RF coil illustrated in FIG. 8 has flexibility and reduced weight and can be compactly folded. As such, the storability and the portability are improved, and operability is also improved.

Modification Example 2

Next, a receiving RF coil according to Modification Example 2 will be described while referencing FIG. 9. With this receiving RF coil, two coils are mounted on the two skeletons 251 and 252.

Specifically, in addition to the first coil 201 of Modification Example 1 illustrated in FIG. 8, the receiving RF coil according to Modification Example 2 includes a third coil 303 that is arranged so as to be adjacent to the first coil 201 in the long axis direction of the skeletons 251 and 252. The third coil 203 is mounted on the first and second skeletons 251 and 252.

The third coil 203 includes a third loop 213 made from a conductor that receives radio frequency signals, and a third signal detector 223 that is inserted in series into the third loop 213 and that detects the signals received by the third loop 213. The third signal detector 223 is mounted on the first skeleton 251 or the second skeleton 252 (in this case, on the first skeleton 251). A portion 233 of the third loop 213 that faces the third signal detector 223 is mounted on skeleton of the first skeleton 251 and the second skeleton 252 on which the third signal detector 223 is not mounted (in this case, on the second skeleton 252).

The first loop 211 and the third loop 213 are arranged such that a portion of each loop overlaps, thereby removing magnetic coupling between the first loop 211 and the third loop 213.

Accordingly, since the number of channels is 2, it is possible to obtain higher sensitivity than with the receiving RF coil illustrated in FIG. 8 in which the number of channels is 1.

A configuration is possible in which three of more coils are arranged on the two skeletons 251 and 252. Such configurations result in further improvements in sensitivity.

Modification Example 3

Figure 10:
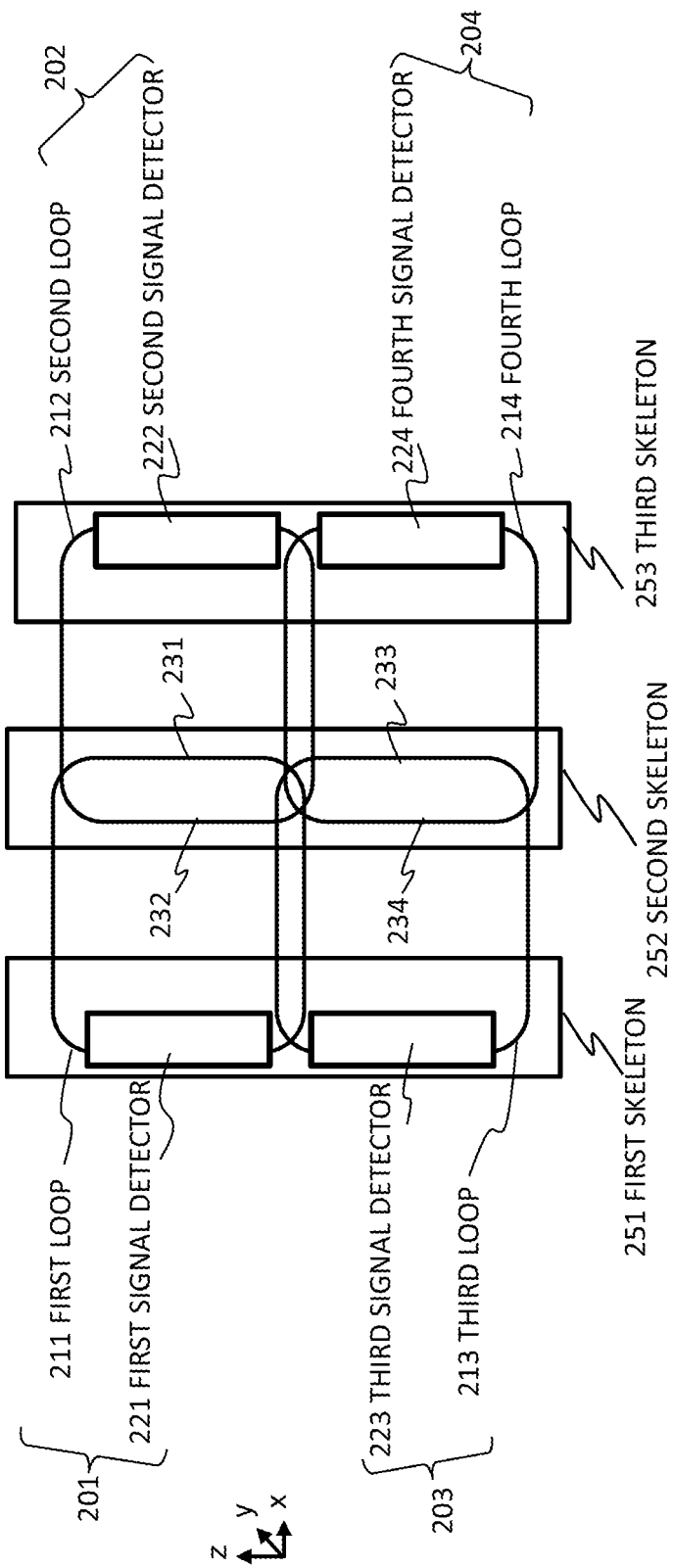
FIG. 10 is a block diagram of a receiving RF coil according to Modified Example 3 of the embodiment.

Next, a receiving RF coil according to Modification Example 3 will be described while referencing FIG. 10. With this receiving RF coil, as illustrated in FIG. 10, four coils 201 to 204 are mounted on the three skeletons 251, 252, and 253. The first and second coils 201 and 202 are arranged as illustrated in FIG. 4. The third coil 203 is arranged as illustrated in FIG. 9.

The fourth coil 204 includes a fourth loop 214 made from a conductor that receives radio frequency signals, and a fourth signal detector 224 that is inserted in series into the fourth loop 214 and that detects the signals received by the fourth loop 214. The fourth signal detector 224 is mounted on the second skeleton 252 or the third skeleton 253 (in this case, on the third skeleton 253). A portion 234 of the fourth loop 214 that faces the fourth signal detector 224 is mounted on the skeleton of the second skeleton 252 and the third skeleton 253 on which the fourth signal detector 224 is not mounted (in this case, on the second skeleton 252).

The first loop 211 and the third loop 213, and the second loop 212 and the fourth loop 214 are arranged such that a portion of each loop overlaps, thereby removing magnetic coupling between the loops.

The number of channels of the receiving RF coil illustrated in FIG. 10 is increased to 4 and, as such, even higher sensitivity can be obtained.

Configurations are possible in which six of more coils are arranged on the four skeletons to obtain even higher sensitivity.

Note that, in the embodiment and the modification examples described above, the loops are constituted by coaxial cables, but the present embodiment is not limited thereto. For example, a single-core cable may be used. In such a case, the weight of the cables that constitute the loops can be reduced to less than when coaxial cables are used and, as such the weight of the receiving RF coil can be reduced even more.

Modification Example 4

Next, a receiving RF coil according to Modification Example 4 will be described while referencing FIG. 11. In the embodiment and the modification examples described above, the portions of the first loop 211 and the second loop 212 on the second skeleton 252 are fixed at positions that overlap as illustrated in FIGS. 4 and 10. However, the present embodiment is not limited to configurations in which the loops are fixed.

Figure 11:
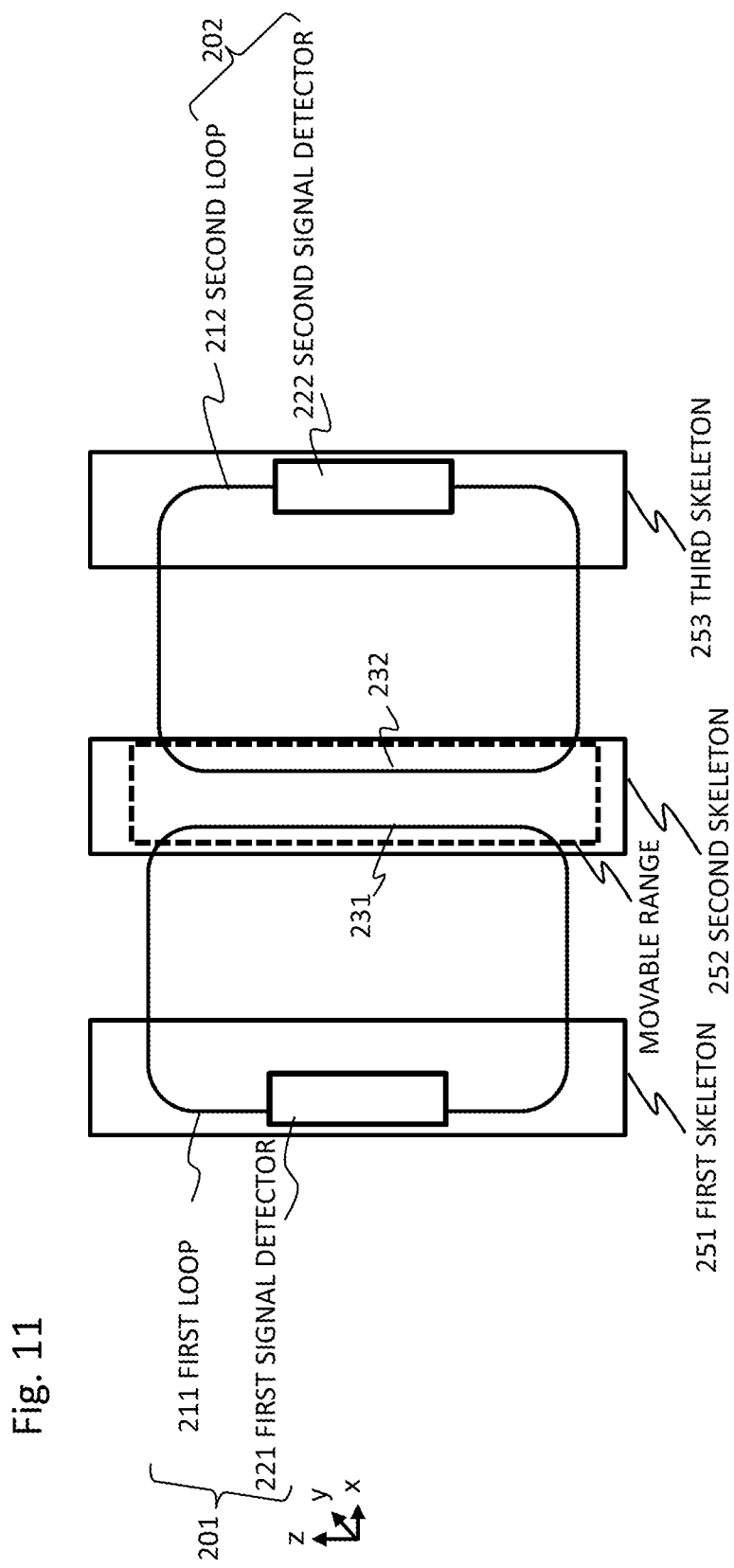
FIG. 11 is a block diagram of a receiving RF coil according to Modified Example 4 of the embodiment.

Specifically, as illustrated in FIG. 11, provided that the environment is such that the effects of magnetic coupling are negligible, a configuration is possible in which the first loop 211 and the second loop 212 are movably mounted in the skeleton 252, and the distance between the first loop 211 and the second loop 212 is increased.

It is possible to change the distance between the second skeleton 252 and the first skeleton 251 and/or the distance between the second skeleton 252 and the third skeleton 253 by changing the amount of overlap between the loops 211 and 212 of the first and second coils.

When the distance between the first loop 211 and the second loop 212 is changed so as to increase, the width of the entire receiving RF coil increases and, as a result, the sensitivity region can be widened.

Note that, in the embodiment and the modification examples described above, a configuration is described in which the skeletons arranged on both ends are not fixed to anything. However, a configuration is possible in which one of these skeletons is connected to the table 102 on which the subject is to be placed. Installing one of the skeletons on the table 102 facilitates operation because an operator can arrange the receiving RF coil on the subject by lifting one of the skeletons, as illustrated in FIG. 1, for example.

When fixing a skeleton to the table 102, a relay skeleton may be inserted between the skeleton and the bed. As a result of this configuration, the width of the entire receiving RF coil, including the relay skeleton, increases, thereby enabling the center of the receiving RF coil to be arranged at a desired position.

Furthermore, a structure is possible in which the receiving RF coil connected to the table can always be arranged on the table by securing storage space on the table in advance. Such a configuration eliminates the need to attach and detach the receiving coil and, as such, improves operability.

As illustrated in FIG. 1, a configuration is possible in which a storage space 102a such as a pocket is provided in a side surface of the table 102 and/or the magnet 110, and the receiving RF coil is stored in the storage space 102a.

DESCRIPTION OF REFERENCE NUMERALS AND SIGNS

71: Cord; 161: Receiving RF (radio frequency) coil; 201, 202, 203, 204: Coil; 211, 212, 213, 214: Loop; 221, 222, 223, 224: Signal detector; 251, 252, 253: Skeleton

What is claimed is:

1. A portable radio frequency coil, comprising:
a first coil, a first skeleton, and a second skeleton, the first skeleton and the second skeleton being rod shaped; wherein
the first coil includes a first loop made from a conductor that receives radio frequency signals, and a first signal detector that is inserted in series into the first loop and that detects the signals received by the first loop;
the first skeleton and the second skeleton are arranged with a spacing in a short axis direction, the first signal detector is mounted on the first skeleton, and a portion of the first loop that faces the first signal detector is mounted on the second skeleton; and
the first loop is deformable, and the spacing between the first skeleton and the second skeleton is changeable in accordance with deformation of the first loop, wherein the radio frequency coil is arranged be folded in a bellows-like manner when not in use.

2. A portable radio frequency coil, comprising:
a plurality of coils that are juxtaposed, and a plurality of skeletons supporting portions of the plurality of coils, the plurality of skeletons being rod shaped; wherein
each of a plurality of the coils includes a loop made from a conductor that receives radio frequency signals, and a signal detector that is inserted in series into the loop and that detects signals received by the loop;
the plurality of skeletons are arranged side by side in a short axis direction thereof with a spacing therebetween;
the signal detectors inserted into each of a plurality of the loop are juxtaposed in the short axis direction of the skeletons with a spacing therebetween, and each of the signal detectors is supported by one of the skeletons; and
the loops are deformable, and the spacing among the plurality of skeletons is changeable in accordance with deformation of the loops,
wherein the radio frequency coil is arranged be folded in a bellows-like manner when not in use.

3. The radio frequency coil according to claim 2, wherein:
the signal detectors and the portions of the loops of all of the coils are respectively supported by the skeletons that are different and adjacent to each other, and
a distance between the skeletons enables the loops to be folded in half.

4. The radio frequency coil according to claim 1, further comprising:
a second coil, and a third skeleton arranged such that long axes of the second skeleton and the third skeleton face each other, the third skeleton being rod shaped; wherein
the second coil includes a second loop made from a conductor that receives radio frequency signals, and a second signal detector that is inserted in series into the second loop and that detects the signals received by the second loop;
the second signal detector is mounted on one of the second skeleton and the third skeleton, and a portion of the second loop that faces the second signal detector is mounted on one of the second skeleton and the third skeleton on which the second signal detector is not mounted; and
the second loop is deformable, and the spacing between the second skeleton and the third skeleton is changeable in accordance with the deformation of the second loop.

5. The radio frequency coil according to claim 1, further comprising a third coil; wherein
the third coil includes a third loop made from a conductor that receives radio frequency signals, and a third signal detector that is inserted in series into the third loop and that detects the signals received by the third loop; and
the third signal detector is mounted on one of the first skeleton and the second skeleton, and a portion of the third loop that faces the third signal detector is mounted on one of the first skeleton and the second skeleton on which the third signal detector is not mounted.

6. The radio frequency coil according to claim 4, further comprising a third coil and a fourth coil; wherein
the third coil includes a third loop made from a conductor that receives radio frequency signals, and a third signal detector that is inserted in series in the third loop and that detects the signals received by the third loop;
the fourth coil includes a fourth loop made from a conductor that receives radio frequency signals, and a fourth signal detector that is inserted in series into the fourth loop and that detects the signals received by the fourth loop;
the third signal detector is mounted on one of the first skeleton and the second skeleton, and a portion of the third loop that faces the third signal detector is mounted on one of the first skeleton and the second skeleton on which the third signal detector is not mounted; and
the fourth signal detector is mounted on one of the first skeleton and the second skeleton, and a portion of the fourth loop that faces the fourth signal detector is mounted on one of the first skeleton and the second skeleton on which the fourth signal detector is not mounted.

7. The radio frequency coil according to claim 4, wherein the first loop and the second loop include a structure or circuitry that removes magnetic coupling between the first loop and the second loop.

8. The radio frequency coil according to claim 7, wherein the first loop and the second loop are arranged such that a portion of the first loop and a portion of the second loop overlap to remove magnetic coupling between the first loop and the second loop.

9. The radio frequency coil according to claim 7, wherein:
a circuit is inserted in series into the first loop and the second loop to remove magnetic coupling between the first loop and the second loop, and
the circuit is mounted on the second skeleton.

10. The radio frequency coil according to claim 1, wherein at least a portion of the first loop that is not mounted on the first skeleton and the second skeleton is a bendable structure.

11. The radio frequency coil according to claim 4, further comprising:
   a drawing mechanism that pulls the first skeleton, the second skeleton, and the third skeleton close and adjacent to each other.

12. The radio frequency coil according to claim 11, wherein the drawing mechanism is a conductor that includes shape memory effects, and forms at least a portion of the first loop and the second loop.

13. The radio frequency coil according to claim 11, wherein the drawing mechanism includes a cord-like member arranged so as to pass through the first skeleton and the second skeleton.

14. The radio frequency coil according to claim 4, wherein:
   the first coil and the second coil are mounted on the second skeleton such that a distance between the first coil and the second coil on the second skeleton can be changed, and
   at least one of a distance between the second skeleton and the first skeleton and a distance between the second skeleton and the third skeleton can be changed.

15. The radio frequency coil according to claim 1, wherein the first skeleton and the second skeleton are members that are bendable in a long axis direction.

16. A magnetic resonance imaging apparatus, comprising the radio frequency coil according to claim 1 as a receiving coil that receives nuclear magnetic resonance signals from a subject.

* * * * *